United States Patent [19]

Czarnek et al.

[11] Patent Number: 5,229,871
[45] Date of Patent: Jul. 20, 1993

[54] OPTICAL DATA LINK FOR COMMUNICATING DATA BETWEEN A STATIONARY MEMBER AND A ROTATING MEMBER AND AN X-RAY COMPUTER TOMOGRAPHY APPARATUS INCORPORATING THE SAME

[75] Inventors: Robert Czarnek, Blacksburg, Va.; Richard Faehnrich, Niles, Ill.

[73] Assignee: Kabushiki Kaisha Toshiba Corporation, Kawasaki, Japan

[21] Appl. No.: 751,542

[22] Filed: Aug. 29, 1991

[51] Int. Cl.5 ............................................. A61B 6/00
[52] U.S. Cl. ..................................... 359/15; 378/4; 378/15; 359/109; 359/154; 359/180; 359/189
[58] Field of Search .................. 378/4, 15, 18, 58, 10, 378/19, 14, 901; 359/109, 154, 180, 189; 250/551

[56] References Cited

U.S. PATENT DOCUMENTS

| | | | |
|---|---|---|---|
| 4,259,584 | 3/1981 | Krumme | 378/15 |
| 4,796,183 | 1/1989 | Ermert et al. | 378/15 |
| 4,996,435 | 2/1991 | Keller | 250/551 |
| 5,018,174 | 5/1991 | Collins | 378/4 |
| 5,029,336 | 7/1991 | Micheron et al. | 378/4 |
| 5,055,821 | 10/1991 | Keller et al. | 378/15 |

FOREIGN PATENT DOCUMENTS 60-108036  6/1985  Japan .

*Primary Examiner*—David P. Porta
*Assistant Examiner*—Kim-Kwok Chu
*Attorney, Agent, or Firm*—Finnegan, Henderson, Farabow, Garrett & Dunner

[57] ABSTRACT

A method and apparatus for optically communicating data between a stationary member and a rotating member, wherein a transmitter, disposed on the rotating member, is provided for transmitting an optical beam therefrom at an angle with respect to the rotating member the angle being fixed during transmission of the optical beam, a receiver, disposed on the stationary member, is provided for receiving the optical beam, and a reflector, disposed on the stationary member, is provided for reflecting the optical beam to the receiver at all times when the optical beam is incident on the reflector.

20 Claims, 8 Drawing Sheets

```
******************PROGRAM "CTSCAN.BAS" *****************
***********************Robert   Czarnek********************
****The Program calculates the shape of a mirror for the
****CT scanner project for BIR
CLS
OPTION BASE 1
defdbl   a-h,k-m,o-z
DIM MIRROR (1000,3)
**************************DATA************************
L=1900
ALFA1=60
ALFA2=100.01
DALFA=0.25
XS=400
YS=850
R=750
EPSO=0.00001
'           INPUT "L      :",L
'           INPUT "ALFA1  :",ALFA1
'           INPUT "ALFA2  :",ALFA2
'           INPUT "DALFA  :",DALFA
'           INPUT "XS     :",XS
'           INPUT "YS     :",YS
'           INPUT "R      :",R
'           INPUT "EPSO   :",EPSO
************** CONVERSION TO RADIANS *****************
PI=3.14159
DEGRAD=PI/180
ALFA1=ALFA1*DEGRAD
ALFA2=ALFA2*DEGRAD
DALFA=DALFA*DEGRAD
XO=R*COS(ALFA1)
**************** CALCULATING THE FIRST POINT *******************
ALFA=ALFA1
C1=(PI-ALFA)*R
C2=1/SIN(ALFA)
C3=R*COS(ALFA)
C4=C2*C2
C5=2* (YS*C2*C3/R-XS-C3*C4)
C6=XS*XS+YS*YS-2*YS*R*C2+R*R*C2*C2
DX=0
X=XO
1001    X=X-DX
DL=L-C1-C2*ABS (X-C3) -SQR (C4*X*X+C5*X+C6)
PRINT X,DL
DX=DL*SIN(ALFA)/2
IF (ABS (DL) > (EPSO/2)) THEN GOTO 1001
Y=-X*C2*C3/R+R*C2
*******************CALCULATING FOLLOWING POINTS*************
N=0
RMAX=0
FOR ALFA=ALFA1 TO ALFA2 STEP DALFA
C1=(PI-ALFA)*R
C2=1/SIN(ALFA)
```

```
            C3=R*COS(ALFA)
            C4=C2*C2
            C5=2*(YS*C2*C3/R-XS-C3*C4)
            C6=XS*XS+YS=YS-2*YS*R*C2+R*R*C2*C2
            AL=SQR((R*COS(ALFA)-X)^2+(R*SIN(ALFA)-Y)^2)
            SA=SQR((XS-X)^2+(YS-Y)^2)
            EPS=((R*COS(ALFA)-X)/AL+(XS-X)/SA)^2+((R*SIN(ALFA)-Y)/AL+(YS-Y)/SA)^2
            EPS=EPSO*0.5*SQR(C4*X*X+C5*X+C6)
            DX=0
            2001    X=X+DX
            DL=L-C1-C2*ABS(X-C3)-SQR(C4*X*X+C5*X+C6)
            DX=DL*SIN(ALFA)/2
            IF      (ABS(DL)>EPS) THEN GOTO 2001
            Y=-X*C2*C3/R+R*C2
            N=N+1
            MIRROR(N,1)=X
            MIRROR(N,2)=Y
            MIRROR(N,3)=ALFA/DEGRAD
            PRINT N, (ALFA/DEGRAD),X,Y
            RPUNKT=SQR(X*X+Y*Y)
            IF   (RPUNKT>RMAX)  THEN RMAX=RPUNKT
            NEXT ALFA
            *******************PLOTTING  THE  CURVE*********************
            CLS
            SCREEN 9
            PICRAD=150                                  'PROMIEN W PUNKTACH
            CIRCLE   (175,175),PICRAD                   'KOLO
            LINE     (0,175)-(639,175)                  'OS POZIOMA
            LINE     (175,0)-(175,349)                  'OS PIONOWA
            CIRCLE   (175+PICRAD*XS/R,175-PICRAD*YS/R*0.75),2,12   'SENSOR
            FOR I=1 TO N
            PX=175+PICARD*MIRROR(I,1)/R
            PY=175-PICRAD*MIRROR(I,2)/R*0.75
            PSET  (PX,PY)                               'LUSTRO
            LINE    (175,175)-(175+PICRAD*COS(ALFA1),175-PICRAD*SIN(ALFA1)*0.75)
            LINE    (175,175)-(175+PICRAD*COS(ALFA2),175-PICRAD*SIN(ALFA2)*0.75)
            NEXT I
            RS=SQR(XS*XS+YS*YS)
            LOCATE 1,60  : PRINT "L     =" : LOCATE 1,66 :PRINT L
            LOCATE 2,60  : PRINT "ALFA1 =" : LOCATE 2,66 :PRINT (ALFA1/DEGRAD)
            LOCATE 3,60  : PRINT "ALFA2 =" : LOCATE 3,66 :PRINT (ALFA2/DEGRAD)
            LOCATE 4,60  : PRINT "DALFA =" : LOCATE 4,66 :PRINT (DALFA/DEGRAD)
            LOCATE 5,60  : PRINT "XS    =" : LOCATE 5,66 :PRINT XS
            LOCATE 6,60  : PRINT "YS    =" : LOCATE 6,66 :PRINT YS
            LOCATE 7,60  : PRINT "R     =" : LOCATE 7,66 :PRINT R
            LOCATE 8,60  : PRINT "EPSO  =" : LOCATE 8,66 :PRINT EPSO
            LOCATE 9,60  : PRINT "RS    =" : LOCATE 9,66 :PRINT RS
            LOCATE 10,60: PRINT "A2-A1 =" : LOCATE 10,66 :PRINT ((ALFA2-ALFA1)/DEGRAD)
            LOCATE 11,60: PRINT "RMAX  =" : LOCATE 11,66 :PRINT RMAX
            LOCATE 12,60: PRINT "PRINT ?" : LOCATE 12,66:INPUT C
            IF C=1 THEN GOTO 3001 ELSE END
            3001        LPRINT "L   =",L
            LPRINT  "ALFA1 =", (ALFA1/DEGRAD)
            LPRINT  "ALFA2 =", (ALFA2/DEGRAD)
            LPRINT  "DALFA =", (DALFA/DEGRAD)
            LPRINT  "XS    =", XS; (XS/25.4),((8*XS/25.4-INT(8*XS/25.4))/8)
            LPRINT  "YS    =", YS, (YS/25.4),((8*YS/25.4-INT(8*YS/25.4))/8)
```

```
LPRINT "R     =", R
LPRINT "EPSO  =", EPSO
LPRINT "RS    =", RS
LPRINT "A2-A1 =", ((ALFA2-ALFA1)/DEGRAD)
LPRINT "RMAX =", RMAX
LPRINT " "
XS="###     ####.##     ####.##     ####.##     ###.###     ###.###     #.###     #.###
      LPRINT"  I    ALFA    X[mm]    Y[mm]    X[in]    Y[in]    Xfr    Yfr"
FOR I=1 TO N
ALFA=MIRROR (I,3)
X=MIRROR (I,1)
Y=MIRROR (I,2)
XI=X/25.4
YI=Y/25.4
XFR=(8*XI-INT(8*XI))/8
YFR=(8*YI-INT(8*YI))/8
LPRINT USING FIS;I,ALFA,X,Y,XI,YI,XFR,YFR
NEXT I
END
```

FIG. 5(c)

OPTICAL DATA LINK FOR COMMUNICATING DATA BETWEEN A STATIONARY MEMBER AND A ROTATING MEMBER AND AN X-RAY COMPUTER TOMOGRAPHY APPARATUS INCORPORATING THE SAME

BACKGROUND OF THE INVENTION

1. Field of the Invention

The present invention relates to a method and apparatus for optically communicating data between a stationary member and a rotating member and, more specifically, to a method and apparatus for optically communicating data between a stationary frame and a rotating ring of an X-ray computer tomography apparatus.

2. Description of the Related Art

Various non-contact techniques have been developed to facilitate the optical transmission of data between a rotating member and a stationary member. Some of these techniques have been applied to X-ray computer tomography apparatuses to provide an optical data link for communicating optical data between a rotating ring and a stationary outside frame of the apparatus.

For example, Keller U.S. Pat. No. 4,996,435 discloses an optical system for transmitting data between a stationary member and a rotating member, such as for transmitting data from the rotating ring in a computer tomography apparatus and the stationary frame of the apparatus. In one embodiment, Keller discloses a frame having a plurality of light transmitters symmetrically mounted thereon. The frame is attached to and rotates with the ring of a tomography apparatus. Each of the light transmitters transmits a fan-shaped beam in a fan plane which is within, or parallel to, the plane defined by the frame, such that the beam transmitted by at least one of the light transmitters is incident upon a stationary light receiver at each rotational position of the frame. In another embodiment, Keller discloses that the light transmitters rotate within and in synchronism with the frame such that the light beams transmitted from the light transmitters follow the light receiver as the frame rotates. A drawback of the systems of both embodiments disclosed by Keller is that, because the light beams are transmitted from the light transmitters in a fan shape, the light receiver must have a sufficiently large surface in order to ensure that a sufficient amount of the light is received. Large light receivers, however, tend to be expensive and have poor frequency response characteristics. Further, in the second embodiment disclosed by Keller, the system requires the use of moving parts which are subject to mechanical failure and tend to increase the cost of the system and its size.

Japanese Patent Disclosure (KOKAI) No. 60-108036 ("the 60-108036 publication") discloses an apparatus for optically transmitting data between a rotary system and a stationary system of an X-ray computer tomography apparatus. In a preferred embodiment, the rotary system comprises a rotor having a pair of optical-axis control means which are pivotably and rotatably supported on the rotor, a pair of decelerating means having teeth which are engageable with teeth of the rotor, a pair of disk-shaped cams, and pair of arms supported by the cams. Attached to each arm is a light transmitting device for transmitting light beams from the rotary system. The rotary system is designed such that, as the rotary system rotates, the angle at which the light transmitting devices transmit beams of light varies in proportion to the rotational movement of the rotary system. As a result, the beams transmitted by the transmitting devices are always convergent on a fixed point on the stationary system. A drawback of the system disclosed in the 60-108036 publication, however, is that it requires the use of moving parts to continuously change the angle of transmission of the light beams. Such parts are subject to mechanical failure and tend to increase the cost of the system and its size.

SUMMARY OF THE INVENTION

Accordingly, it is an object of the present invention to provide a cost-effective and efficient method and apparatus for optically communicating data between a stationary member and a rotating member.

It is another object of the present invention to provide a cost-effective and efficient method and apparatus for optically communicating data between a stationary frame and a rotating ring of an X-ray computer tomography apparatus.

Additional objects and advantages of the invention will be set forth in the description which follows, and in part will be obvious from the description, or may be learned by practice of the invention.

To achieve the foregoing objectives, an optical data link for communicating data between a stationary member and a rotating member is provided, comprising a transmitter disposed on the rotating member for transmitting an optical beam at an angle with respect to the rotating member the angle being fixed during transmission of the optical beam, a receiver disposed on the stationary member for receiving the optical beam, and a reflector disposed on the stationary member for reflecting the optical beam to the receiver at all times when the optical beam is incident on the reflector.

In a preferred embodiment, the reflector comprises a mirror which reflects the optical beam according to an angular position of the rotating member, with respect to the stationary member and the transmitter comprises a laser diode.

Further, the transmitter can comprise a plurality of laser diodes arranged along a circumference of the rotating member, wherein each of the laser diodes transmits an optical beam and the reflector simultaneously reflects optical beams transmitted by one or more of the laser diodes.

Still further, the reflector can comprise a single or double curvature mirror, and the optical data link can include a lens or other device for focusing or collimating the optical beam transmitted by the transmitter onto the reflector.

BRIEF DESCRIPTION OF THE DRAWINGS

The accompanying drawings, which are incorporated in and constitute a part of the specification, illustrate the presently preferred apparatuses and method of the invention and, together with the general description given above and the detailed description of the preferred embodiments given below, serve to explain the principles of the invention. Of the drawings:

FIGS. 5(a)-5(c) are a computer program listing used for calculating the shape of the mirror shown in FIG. 1;

DESCRIPTION OF THE PREFERRED EMBODIMENTS AND METHOD

Figure 1:
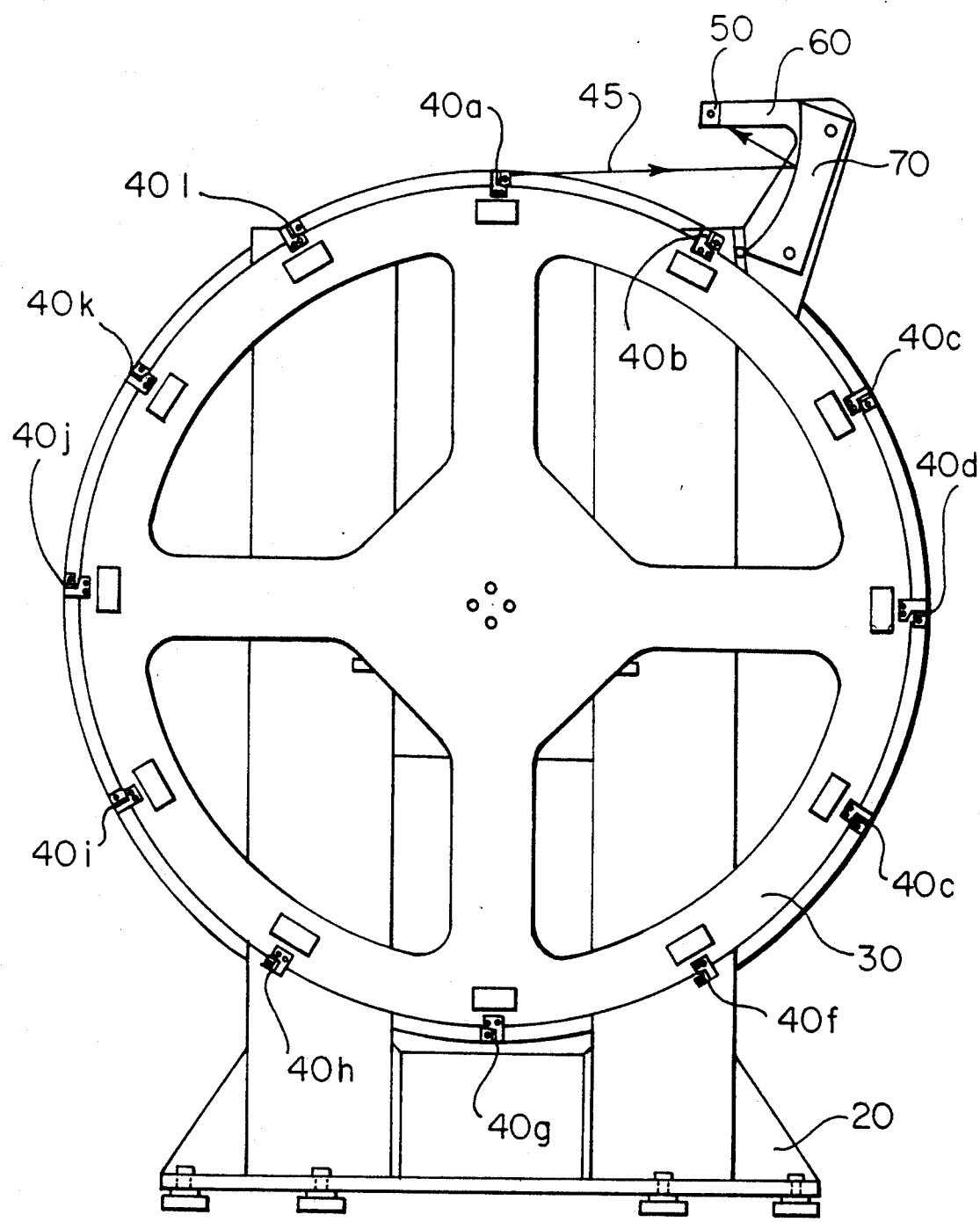
FIG. 1 is an illustration of a test fixture which operates in accordance with the teachings of the present invention.

Reference will now be made in detail to the presently preferred apparatuses and method incorporating the invention as illustrated in the accompanying drawings, in which like reference characters designate like or corresponding parts throughout the several drawings.

As shown in FIG. 1, there is provided a test fixture 10 which comprises a frame assembly 20, a rotating assembly 30, a plurality of transmitter assemblies 40a-40l, a receiver assembly 50, a mounting member 60, and a mirror 70.

The plurality of transmitter assemblies 40a-40l are positioned at points along the outside perimeter of the rotating assembly 30 and each is capable of transmitting an optical beam 45 representing, for example, digital or analog data, at a selected angle with respect to the rotating assembly 30, as shown in FIG. 1. As will become apparent from the detailed description that follows, the number of transmitter assemblies, their positions along the perimeter of the rotating assembly 30, and the angle at which the optical beams are transmitted can be varied to optimize performance, complexity, and cost of the test fixture 10.

The rotating assembly 30 is mounted onto the frame assembly 20 such that the rotating assembly 30 rotates about its central axis. Because the transmitter assemblies 40a-40l are secured to the rotating assembly 30, as described above, the transmitter assemblies 40a-40l rotate with the rotating assembly 30. The receiver assembly 50 and the mirror 70 are secured to the mounting member 60 which, in turn, is secured to the frame assembly 20. Accordingly, the receiver assembly 50, mounting member 60, and mirror 70 remain stationary with respect to the rotating assembly 30 and transmitter assemblies 40a-40l. Further, the rotating assembly 30 has, at any given moment, an instantaneous angular position with respect to the frame assembly 20. Likewise, each of the transmitter assemblies 40a-40l also has, at any given moment, an instantaneous angular position with respect to the receiver assembly 50.

Figure 2:
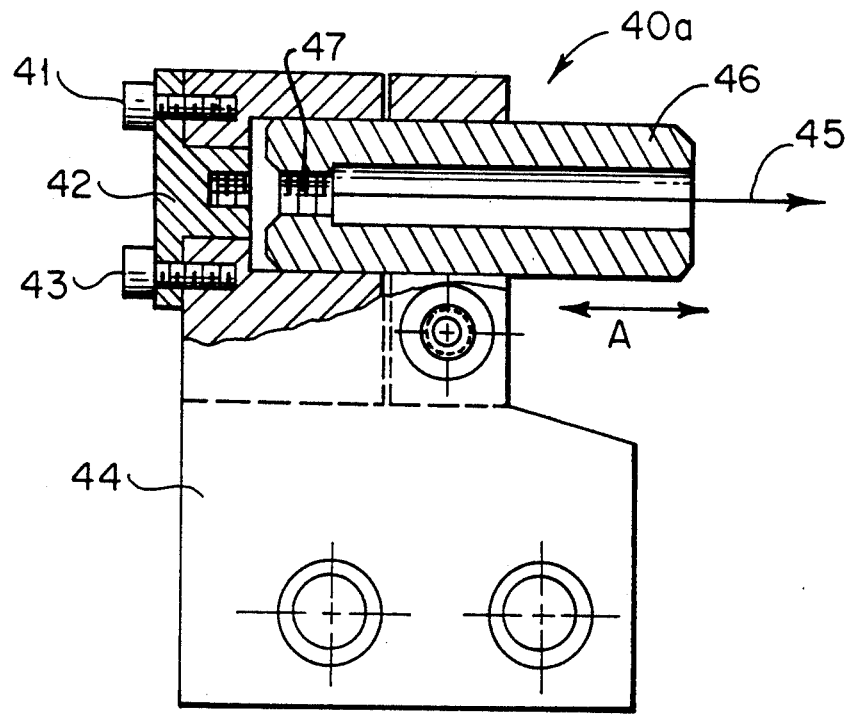
FIG. 2 is an illustration of the transmitter assembly of the test fixture shown in FIG. 1.

As shown in FIG. 2, each of the transmitter assemblies 40a-40l preferably comprises a laser diode 42 mounted to a base 44 via screws 41 and 43 which, when driven by a driver circuit (which will be described later), transmits an optical beam 45. In place of the laser diode 42, each of the transmitter assemblies 40a-40l can comprise an LED or other light source. However, it is preferable that the light source is capable of being modulated such that it can be encoded with digital or analog data.

As will be described later, each of the transmitter assemblies 40a-40l can also comprise a collimating lens 47 held in position by a lens holder 46. The lens holder 46 can be adjusted along its central axis A such that the optical beam 45 is collimated or properly focused. Finally, the entire transmitter assembly is secured to the rotating assembly 30 at its base 44. It should be noted that the angle at which the optical beam 45 is transmitted can be adjusted, for example, by adjusting the positioning of the transmitter assembly on the rotating assembly. However, during operation of the test fixture 10, for example, during transmission of the optical beam 45, the angle at which the optical beam 45 is transmitted remains fixed.

Figure 3:
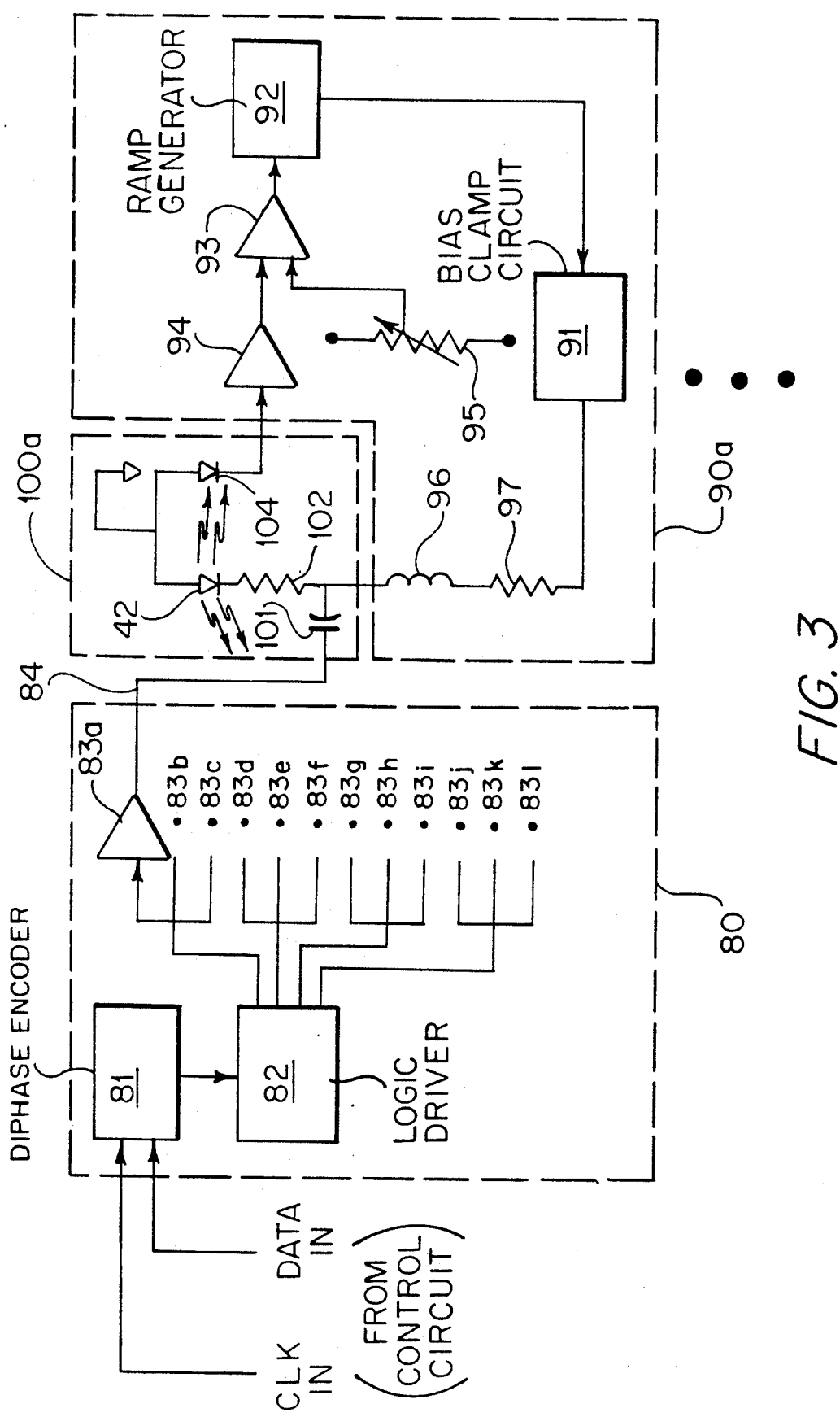
FIG. 3 illustrates a simplified diagram of the electronic circuits used in conjunction with the transmitter assembly shown in FIG. 2.

FIG. 3 illustrates a driver circuit 80 for driving the transmitter assemblies 40a-40l. As shown in the figure, the driver circuit 80 comprises a diphase encoder 81, a logic driver 82, and a plurality of pulse amplifiers 83a-83l. The driver circuit 80 is controlled via CLK IN and DATA IN signals generated by a control circuit (not shown) such as a microprocessor or computer. Each of the pulse amplifiers 83a-83l is coupled via a coaxial cable 84 to a corresponding one of a plurality of laser diode circuits 100a-100l each of which comprises a laser diode 42, a photodiode 104, an impedance matching resistor 102, and a capacitor 101. Preferably, the impedance of the impedance matching resistor 102 is matched with the impedance of the coaxial cable 84 to enable remote control of the laser diode circuits 100a-100l by the driver circuit 80 with minimal power loss. Further, each of the laser diode circuits 100a-100l is coupled to a corresponding one of a plurality of bias circuits 90a-90l, each of which comprises a bias clamp circuit 91, a ramp generator 92, a differential amplifier 93, a transimpedance amplifier 94, a bias set-point adjust resistor 95, a bias choke 96, and a bias resistor 97.

As the rotating assembly 30 rotates about its central axis, the control circuit generates CLK IN and DATA IN signals such that the logic driver 82 drives the pulse amplifiers 83a-83l. Each of the pulse amplifiers 83a-83l drives a laser diode 42 of a corresponding one of the laser diode circuits 100a-100l. A portion of the light transmitted by the energized laser diode 42 is received by the photo diode 104 and converted into a feedback signal. This feedback signal drives a corresponding one of the bias circuits 90a-90l to control the bias of the laser diode 42. Another portion of the light transmitted by the energized laser diode 42 is transmitted as a beam of light from the transmitter assembly. Alternatively, the light can first be collimated by a collimating lens and then transmitted from the transmitter assembly as a collimated optical beam, as described above with regard to FIG. 2.

In this manner, the transmitter assemblies 40a-40l are controlled such that each transmits an optical beam, at least one of which reaches the mirror 70 at any given time. Preferably, the optical beams are transmitted along a line tangent to the rotating assembly 30 to minimize the space requirements of the system. Further, all of the transmitter assemblies 40a-40l need not simultaneously transmit an optical beam. For example, the pulse amplifiers 83a-83l can be multiplex-driven by the logic driver 82 such that only selected ones of the transmitter assemblies 40a-40l transmit an optical beam at any one time.

As should be apparent from the geometries of the test fixture 10, the optical beam transmitted by any one of the transmitter assemblies 40a-40l will only reach the mirror 70 while the rotating assembly 30 is within a certain range of angular positions. As should also be apparent, the range of contact of an optical beam on the mirror 70 is a function of the number of transmitter assemblies and the position and size of the mirror 70. The larger the mirror 70, the larger the range of contact and the smaller the number of transmitter assemblies required to ensure continuous contact of an optical beam and the mirror 70. However, it should be noted that, as the number of transmitter assemblies is decreased, the size of the mirror 70 can increase to ensure continuous contact, thereby increasing the size and cost of the test fixture 10. In theory, it is possible to have a system that requires only a single transmitter assembly. Such a system, however, would require an unreasonably large mirror (the mirror would have to extend the entire perimeter of the rotating assembly). In practice, however, a compromise between the number of transmitter assemblies and the size of the mirror 70 must be made to accommodate size and cost constraints. Further, to ensure continuous contact of an optical beam on the mirror 70, the transmitter assemblies 40a–40l can be positioned along the perimeter of the rotating assembly 30 such that the beams from adjacent ones of the transmitter assemblies 40a–40l both reach the mirror 70 at any time.

In situations where continuous contact of an optical beam on the mirror 70 is not necessary, the number of transmitter assemblies can be reduced without increasing the size of the mirror 70. In such a situation, it may be desirable to store data contained in the optical beams in a memory device during times when no beams reach the mirror 70.

To ensure continuity of transmission of data from the mirror 70 to the receiver assembly 50 throughout the range of angular positions at which an optical beam transmitted by a transmitter assembly reaches the mirror 70, the shape of the mirror 70 at any given point along its surface is such that any optical beam which reaches the mirror 70 is reflected onto the receiver assembly 50. To achieve this result, the shape of the mirror 70 must vary according to the instantaneous angular position of the rotating assembly 30.

Figure 6:
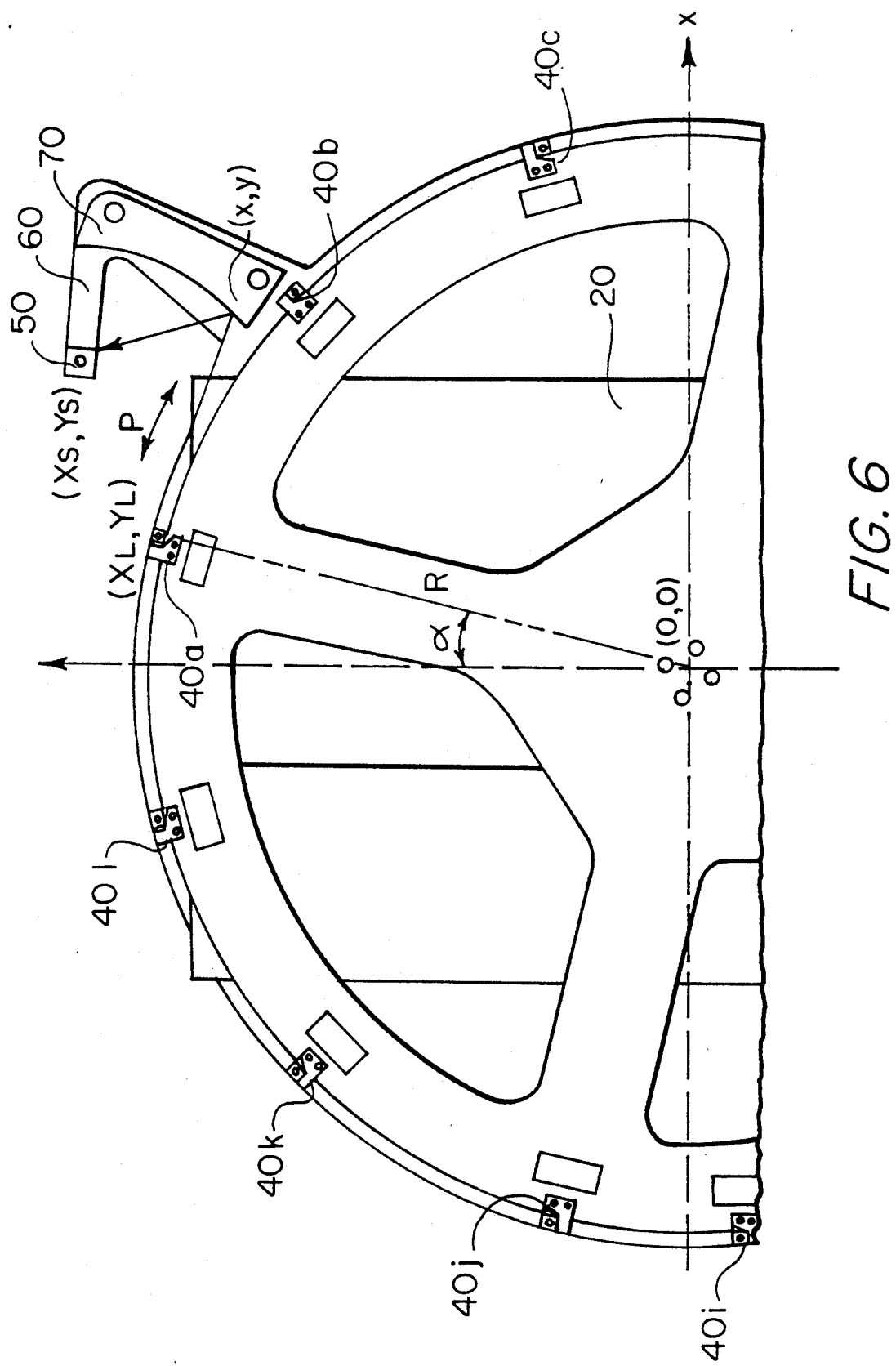
FIG. 6 illustrates the relationship between the parameters used in calculating the shape of the mirror shown in FIG. 1.

In one embodiment, the mirror 70 comprises a single curvature mirror having a curvature in the plane of the rotating assembly 30. The mirror 70 is piecewise elliptical, as will be explained later, and its curvature is described by the following system of equations, as illustrated in FIG. 6:

$$y = -x(\cos\alpha/\sin\alpha) + (R/\sin\alpha) \quad (1)$$

$$l = (\pi - \alpha)R + (1/\sin\alpha)(|x - R\cos\alpha|) + \quad (2)$$
$$\{(x^2/\sin^2\alpha) + 2x[y_s(\cos\alpha/\sin\alpha) - x_s - R(\cos\alpha/\sin^2\alpha)] +$$
$$[x_s^2 + y_s^2 - 2y_s(R/\sin\alpha) + (R^2/\sin^2\alpha)]\}^{\frac{1}{2}}$$

Equation (1) defines a line p tangent to the rotating assembly 30 that has a radius R, at a point on the circle defined by an angle $a$ measured clockwise from the y-axis, as follows:

$$p: 0 = (x - x_L)\cos\alpha + (y - y_L)\sin\alpha \quad (1a)$$

where x and y are the coordinates of a point on the mirror 70, l is the length of the optical path along which the optical beam travels, $x_L$ and $y_L$ are the coordinates of the transmitter assembly transmitting the optical beam, and $a$ and R are the polar coordinates of the transmitter assembly. Therefore, equation (1) can be derived as follows:

$$y = -x(\cos\alpha/\sin\alpha) + y_L + x_L(\cos\alpha/\sin\alpha) \quad (1b)$$

$$= -x(\cos\alpha/\sin\alpha) + R\sin\alpha + R(\cos^2\alpha/\sin\alpha) \quad (1c)$$

$$= -x(\cos\alpha/\sin\alpha) + (R/\sin\alpha) \quad (1d)$$

Figure 8:
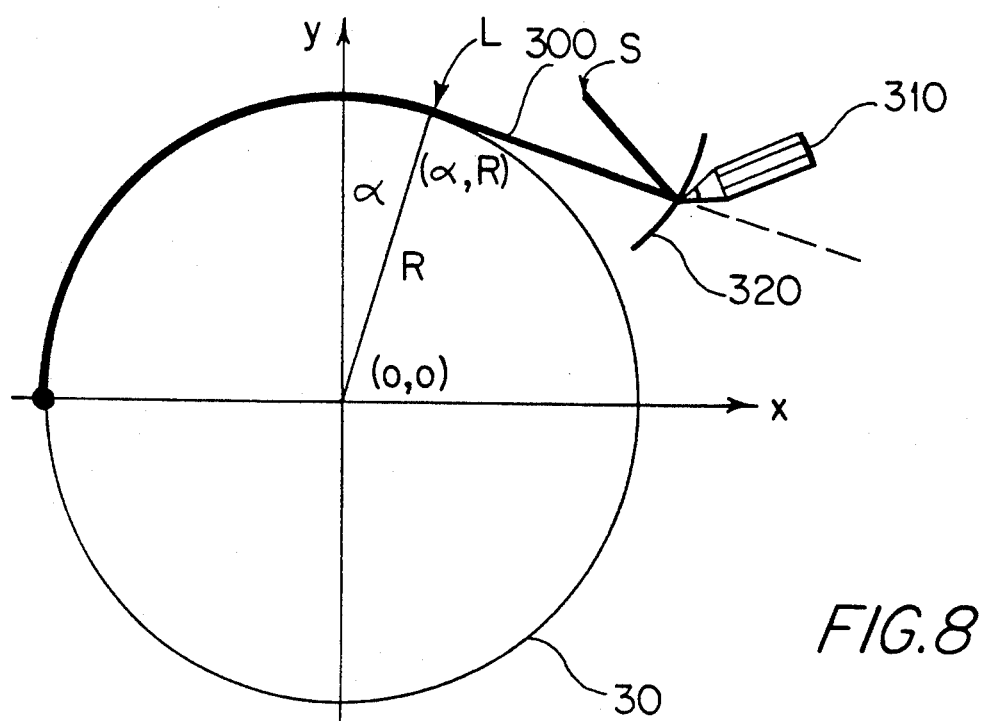
FIG. 8 illustrates a technique for constructing a curve representing the shape of the mirror shown in FIG. 1.

Equation (2) is based on the same logic as the construction of an ellipse with a piece of string secured at two points. If light is transmitted from one of these points, it will be focused on the other. In the present invention, however, an elliptical mirror can not be used because the transmitter assemblies 40a–40l are moving. However, as explained above, throughout a range of angular positions, it is desired that an optical beam transmitted by at least one of the transmitter assemblies 40a–40l be reflected towards the receiver assembly 50. More precisely, it is desired that an optical beam transmitted by a transmitter assembly be directed towards a point in space. As illustrated in FIG. 8, following the logic behind an elliptical mirror, the curve that will satisfy the above requirements can be constructed with a string 300 that has one end secured to the rotating assembly 30 at some point L, for example, the point that has polar coordinates $(\alpha, R)$, and the other end secured at some point S outside of the rotating assembly 30. The string 300 is wrapped around the rotating assembly 30 and stretched with a pencil 310. If the pencil 310 is moved in such a way that the string 300 is subjected to constant tension, it will draw a curve 320 defining the desired curvature of the mirror 70. Point S will be the point where the receiver assembly 50 can be located and point L is the instantaneous position of the transmitter assembly transmitting the optical beam.

Mathematically, the condition that the sum of the distance measured along the perimeter of the wheel from point $(\pi, R)$ to point L, the distance from L to A, and the distance from point A to point S is constant. Point A is the point of an instantaneous position of the pencil and, as such, is a point on the mirror 70. The constant 1 corresponds to the length of the string, as follows:

$$1 = (\pi - \alpha)R + LA + AS \quad (2a)$$

$$= (\pi - \alpha)R + [(x - R\cos\alpha)^2 + \quad (2b)$$
$$(y - R\sin\alpha)^2]^{\frac{1}{2}} + [(x_s - x)^2 + (y_s - y)^2]^{\frac{1}{2}}$$

$$= (\pi - \alpha)R + [x^2 - 2Rx\cos\alpha + R^2\cos^2\alpha + \quad (2c)$$
$$y^2 - 2Ry\sin\alpha + R^2\sin^2\alpha]^{\frac{1}{2}} +$$
$$[x_s^2 - 2xx_s + x^2 + y_s^2 - 2yy_s + y^2]^{\frac{1}{2}}$$

Equations (1) and (2c) form a parametric system of equations describing the curvature of the mirror 70. By substitution, this system of equations can be reduced to one parametric function that can be solved for x as a function of $\alpha$. The values of x and $\alpha$ can then be substituted into equation (1), from which the corresponding value of y can be calculated, as follows:

$$1 = \pi - \alpha)R + [x^2 + x^2(\cos^2\alpha/\sin^2\alpha) - \quad (2d)$$
$$2x(R\cos\alpha/\sin^2\alpha) + (R^2/\sin^2\alpha - 2Rx\cos\alpha +$$
$$2Rx(\cos\alpha/\sin\alpha)\sin\alpha - 2R^2(\sin\alpha/\sin\alpha) + R^2]^{\frac{1}{2}} +$$
$$[x_s^2 - 2xx_s + x^2 + y_s^2 + 2y_sx(\cos\alpha/\sin\alpha) -$$
$$2y_s(R/\sin\alpha) + x^2(\cos^2\alpha/\sin^2\alpha) -$$

-continued $$= (\pi - \alpha)R + [(x^2/\sin^2\alpha) - x2R(\cos\alpha/\sin^2\alpha) + \quad (2e)$$
$$2Rx(\cos\alpha/\sin^2\alpha) + (R^2/\sin^2\alpha)]^{\frac{1}{2}}$$
$$R^2(\cos^2\alpha/\sin^2\alpha)]^{\frac{1}{2}} + \{(x^2/\sin^2\alpha) +$$
$$x2[y_s(\cos\alpha/\sin\alpha) - x_s - R(\cos\alpha/\sin^2\alpha)] +$$
$$x_s^2 + y_s^2 = 2y_s(R/\sin\alpha) + (R^2/\sin^2\alpha)\}^{\frac{1}{2}}$$

$$= (\pi - \alpha)R + (1/\sin\alpha)(|x - R\cos\alpha|) + \quad (2e)$$
$$\{(x^2/\sin^2\alpha) + 2x[y_s(\cos\alpha/\sin\alpha) - x_s -$$
$$R(\cos\alpha/\sin^2\alpha)] + [x_s^2 + y_s^2 - 2y_s(R/\sin\alpha) + (R^2/\sin^2\alpha)]\}^{\frac{1}{2}}$$

It should be noted that equations (1) and (2) assume that each optical beam is transmitted along a line tangent to the rotating assembly 30, i.e., at an angle of 90° with respect to a radius of the rotating assembly 30 extending from its central axis to the transmitter assembly transmitting the optical beam.

With a single curvature mirror having a shape defined by equations (1) and (2), however, if the optical beams transmitted from the transmitter assemblies 40a-40l are slightly diverging, then the optical beam, when reflected from the mirror 70 onto the receiver assembly 50, will be focused into a band rather than a point with the direction of the band extending perpendicular to the plane of the rotating assembly 30. The width of the band is caused by the fact that the mirror deviates from an elliptical shape which causes aberration of the light beam. Thus, the larger the divergence of the optical beam, the wider the band. A result is that a portion of the optical beam is not received by the receiver assembly 50, thereby decreasing the efficiency of the system. One method of overcoming this problem is to provide each of the transmitting assemblies with a focusing lens such as the collimating lens 47 shown in FIG. 2. This solution, however, introduces as many extra optical elements as there are transmitting assemblies and, because precise alignment of these elements is crucial, it significantly increases both the complexity and cost of the system.

To overcome the above-identified problems associated with a single curvature mirror, in another embodiment, the mirror 70 comprises a double curvature mirror having a first curvature, in the plane of the rotating assembly 30, described by equations (1) and (2) above, and a second curvature, in a plane perpendicular to the plane of the rotating assembly 30, described by the following equation:

$$r = [2(\overline{AL} \cdot \overline{V_n})(\overline{AS} \cdot \overline{V_n})]/(\overline{AI} + \overline{AS}) \cdot \overline{V_n}] \quad (3)$$

Equation (3) is derived from the following cylindrical mirror equation:

$$(1/l_o) + (1/l_i) = (1/f) = (2/r) \quad (3a)$$

where f is the focal length of the mirror 70 and r is the radius of curvature of the mirror 70. It follows that:

$$r = 2l_o l_i/(l_o + l_i); \text{ and} \quad (3b)$$
$$r = [2(\overline{AL} \cdot \overline{V_n})(\overline{AS} \cdot \overline{V_n})]/[(\overline{AL} + \overline{AS}) \cdot \overline{V_n}] \quad (3c)$$

where $\overline{V}$ is the vector normal to the surface of the mirror 70 at point A. It further follows that:

$$\overline{V_n} = \overline{AL}/|\overline{AL}| + \overline{AS}/|\overline{AS}|; \quad (3d)$$
$$\overline{AL}/|\overline{AL}| = (x_L - x; y_L - y)/[(x_L - x)^2 + (y_L - y)^2]^{\frac{1}{2}}; \quad (3e)$$
$$\overline{AS}/|\overline{AS}| = (x_S - x; y_S - y)/[(x_S - x)^2 + y_S - y)^2]^{\frac{1}{2}}; \quad (3f)$$
$$V_{nx} = (x_L - x)/[(x_L - x)^2 + (y_L - y)^2]^{\frac{1}{2}} + \quad (3g)$$
$$(x_S - x)/[(x_S - x)^2 + (y_S - y)^2]^{\frac{1}{2}}; \text{ and}$$
$$V_{ny} = (y_L - x)/[(x_L - x)^2 + (y_L - y)^2]^{\frac{1}{2}} + \quad (3h)$$
$$(y_S - x)/[(x_S - x)^2 + (y_S - y)^2]^{\frac{1}{2}}$$

where $V_{nx}$ and $V_{ny}$ are the scalar components of vector $V_n$.

One benefit of using a double curvature mirror is that the optical beams transmitted by the transmitter assemblies need not be focused at their sources. Instead, focusing of the beams can be accomplished at the surface of mirror 70 thereby eliminating the need for placing focusing lenses at each of the transmitter assemblies. Nevertheless, in both embodiments, preferably, the optical beam reflected from mirror 7 is a collimated optical beam.

FIGS. 5(a)-5(c) illustrate a sample computer program listing used for calculating the shape of the mirror 70. Modifications of the program can be made to tailor the program to any specific application of the present invention, as should be obvious to one skilled in the art.

Figure 4:
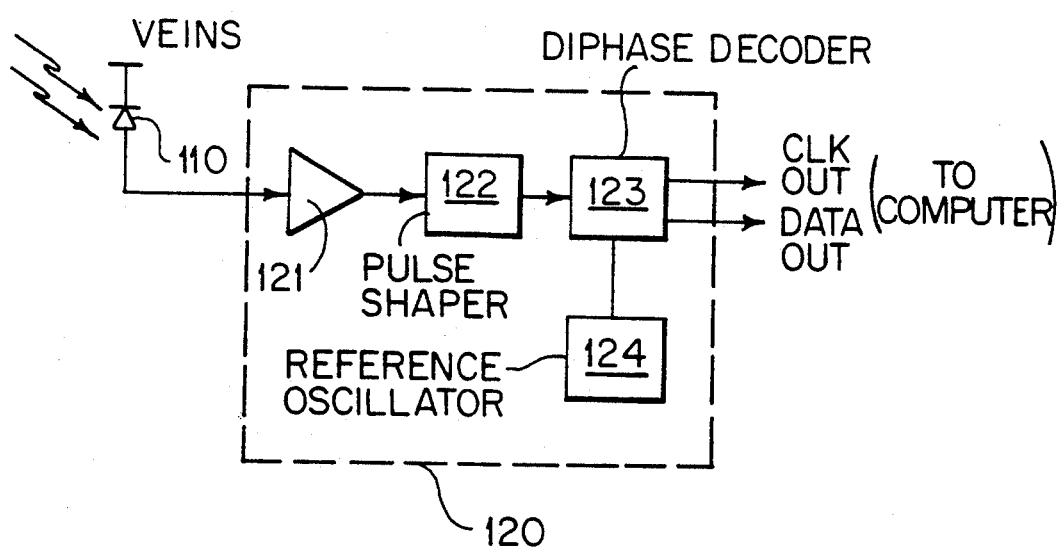
FIG. 4 illustrates a simplified diagram of the electronic circuits used in conjunction with the receiver assembly shown in FIG. 1.

FIG. 4, illustrates the electronic circuitry used in connection with the receiver assembly 50. As shown in the figure, the circuitry comprises a photodiode 110, having a bias voltage $V_{BIAS}$ applied thereacross, and a receiver circuit 120. The receiver circuit 120 includes a transimpedance amplifier 121, a pulse shaper 122, a diphase decoder 123, and a reference oscillator 124.

Photodiode 110 receives optical beams reflected from the mirror 70 and converts the optical beams into electrical signals. The electrical signals are then processed by the receiver circuit 120 into DATA OUT and CLK OUT signals. The DATA OUT and CLK OUT signals can then be processed by, for example, a computer (not shown). Because the optical beams reflected from mirror 70 are collimated, photodiode 110 need not be very large. Thus, photodiode 110 can be inexpensive and yet have good frequency response characteristics.

Figure 7:
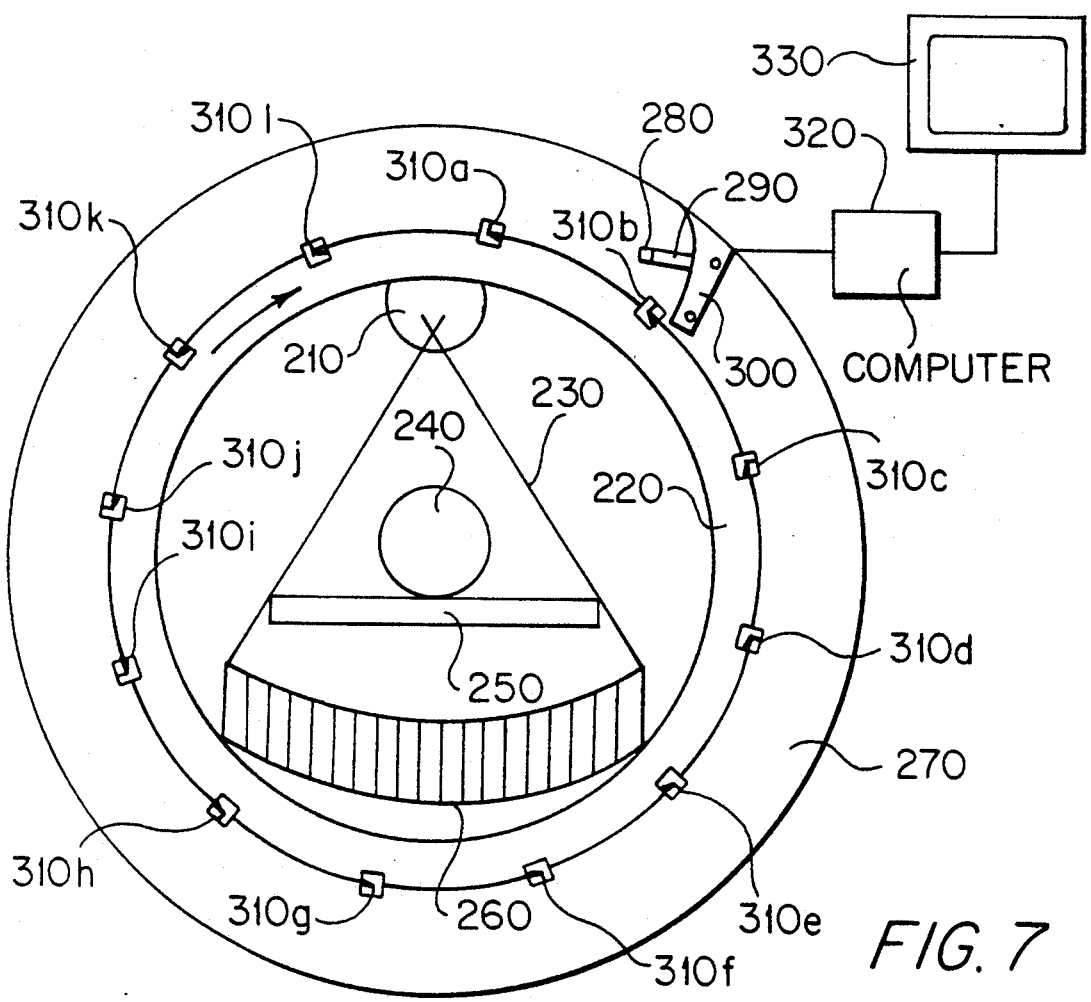
FIG. 7 illustrates an X-ray computer tomography apparatus incorporating the teachings of the present invention.

Finally, FIG. 7 illustrates an X-ray computer tomography apparatus incorporating the teachings of the present invention. As shown in FIG. 7, X-ray computer tomography apparatus 200 comprises a radiation source 210, a platform 250, a ring 220, a detector array 260, a stationary frame 270, a receiver assembly 280, a mounting member 290, a mirror 300, a plurality of transmitter assemblies 310a-310l, a computer 320, and a display 330.

As the ring 220 rotates about the object 240, the radiation source 210, which comprises, for example, an X-ray tube, generates a fan-shaped beam of X-rays 230 which penetrate the object 240 resting on the platform 250. Radiation from the X-rays is detected by the detector array 260. The detector array 260 converts the detected radiation into electrical signals which represent the intensity of the detected radiation.

The electrical signals are converted into optical beams by the transmitter assemblies 310a-310l and the optical beams are reflected by the mirror 300 onto the receiver 280, in a manner as set forth above with regard to the test fixture 10 of FIG. 1. The optical beams received by the receiver 280 are then converted into electrical signals, processed by the computer 320, and displayed on the display 330 as a tomographic image.

As should be apparent from the above description of the present invention, the present invention has many advantages over the prior art. For example, in theory, with a mirror manufactured with high precision and light sources transmitting narrow beams of light, nearly all of the light from the optical beams transmitted by each transmitter assembly and reflected by the mirror can be directed to the receiver assembly. In practice, however, one can typically allow some tolerances for manufacturing and assembly of the system, such that at least about 1% of the light from each optical beam can be collected by the receiver assembly. With this level of efficiency, small, low-powered, and inexpensive light sources can be used, thereby decreasing the size and cost of the system.

Additional advantages and modifications will readily occur to those skilled in the art. Therefore, the invention in its broader aspects is not limited to the specific details, representative devices, and illustrative examples shown and described. Accordingly, departures may be made from such details without departing from the spirit or scope of the general inventive concept as defined by the appended claims and their equivalents.

What is claimed is:

1. An optical data like apparatus for communicating data between a stationary member and a rotating member, comprising:
   transmitting means disposed on the rotating member for transmitting an optical beam therefrom at an angle with respect to the rotating member, the angle being fixed during transmission of the optical beam;
   receiving means disposed at a fixed point on the stationary member for receiving the optical beam; and
   reflecting means disposed on the stationary member for reflecting the optical beam to the receiving means at all times when the optical beam is incident on the reflecting means.

2. The optical data link according to claim 1, wherein the reflecting means is a single curvature mirror having a curvature described by the equations:

$$y = -x(\cos\alpha/\sin\alpha) + (R/\sin\alpha) \quad (1)$$

$$l = (\pi - \alpha)R + (1/\sin\alpha)(|x - R\cos\alpha|) + \quad (2)$$
$$\{(x^2/\sin^2\alpha) + 2x[y_s(\cos\alpha/\sin\alpha) - x_s - R(\cos\alpha/\sin^2\alpha)] +$$
$$[x_s^2 + y_s^2 = 2y_s(R/\sin\alpha) + (R^2/\sin^2\alpha)\}^{\frac{1}{2}}$$

3. The optical data link according to claim 1, wherein the reflecting means is a double curvature mirror having a first curvature in a first plane described by the equations:

$$y = -x(\cos\alpha/\sin\alpha) + (R/\sin\alpha) \quad (1)$$

$$l = (\pi - \alpha)R + (1/\sin\alpha)(|x - R\cos\alpha|) + \quad (2)$$
$$\{(x^2/\sin^2\alpha) + 2x[y_s(\cos\alpha/\sin\alpha) - x_s - R(\cos\alpha/\sin^2\alpha)] +$$
$$[x_s^2 + y_s^2 = 2y_s(R/\sin\alpha) + (R^2/\sin^2\alpha)\}^{\frac{1}{2}}$$

and a second curvature in a second plane perpendicular to the first plane described by the equation:

$$r = [2(\overline{AL} \cdot \overline{V_n})(\overline{AS} \cdot \overline{V_n})]/(\overline{AI} + \overline{AS}) \cdot \overline{V_n}] \quad (3)$$

4. An X-ray computer tomography apparatus having a radiation source disposed on a rotating member for irradiating an object, a radiation detector disposed on the rotating member such that the object is positioned between the radiation detector and the radiation source for detecting radiation penetrating the object and for generating an electrical signal proportional to the intensity of the detected radiation, and a stationary member, the X-ray computer tomography apparatus including an optical link apparatus comprising:
   transmitting means disposed on the rotating member for converting the electrical signal into an optical beam and for transmitting the optical beam therefrom at an angle with respect to the rotating member the angle being fixed during transmission of the optical beam;
   receiving means disposed on the stationary member for receiving the optical beam; and
   reflecting the optical beam to the receiving means at all times when the optical beam is incident on the reflecting means.

5. The according to claim 1 or 4, wherein the reflecting means reflects the optical beam according to an angular position of the rotating member with respect to the stationary member.

6. The apparatus according to claim 1 or 4, wherein the transmitting means comprises a laser diode or LED.

7. The apparatus according to claim 1 or 4, wherein the transmitting means comprises a plurality of laser diodes arranged along a circumference of the rotating member, each of the laser diodes transmitting an optical beam at an angle with respect to the rotating member the angle being fixed during transmission of the optical beam.

8. The apparatus according to claim 1 or 4, wherein the receiving means comprises a photodiode.

9. The apparatus according to claim 1 or 4, wherein said transmitting means comprises a laser diode circuit for transmitting said optical beam, a driver circuit remotely driving said laser diode circuit, and a bias circuit for controlling a bias of said laser diode circuit.

10. A method for communicating data between a stationary member and a rotating member, the method comprising the steps of:
    transmitting an optical beam from the rotating member at an angle with respect to the rotating member, the angle being fixed during transmission of the optical beam;
    receiving the optical beam at a fixed point on the stationary member; and
    reflecting the optical beam off of a reflective surface disposed on the stationary member to the fixed point on the stationary member at all times when the optical beam is incident on the reflective surface.

11. The method according to claim 10, wherein the step of transmitting the optical beam includes the step of transmitting a plurality of optical beams from corresponding points on the periphery of the rotating member at angles with respect to the rotating member, the angles being fixed during transmission of the optical beams, and wherein the step of reflecting the optical beam includes the step of simultaneously reflecting one or more of the plurality of optical beams to the stationary member according to an angular position of the rotating member with respect to the stationary member.

12. An optical data link for communicating data between a stationary member and a rotating member, comprising:
   transmitting means disposed on the rotating member for transmitting an optical beam therefrom at an angle with respect to the rotating member, the angle being fixed during transmission of the optical beam;
   receiving means disposed at a fixed point on the stationary member for receiving the optical beam; and
   a mirror disposed on the stationary member, the mirror reflecting the optical beam to the receiving means at all times when the optical beam is incident on the mirror.

13. An X-ray computer tomography apparatus having a radiation source disposed on a rotating member for irradiating an object, a radiation detector disposed on the rotating member such that the object is positioned between the radiation detector and the radiation source for detecting radiation penetrating the object and for generating an electrical signal proportional to the intensity of the detected radiation, and a stationary member, the X-ray computer tomography apparatus comprising:
   transmitting means disposed on the rotating member for converting the electrical signal into an optical beam and for transmitting the optical beam therefrom at an angle with respect to the rotating member, the angle being fixed during transmission of the optical beam;
   receiving means disposed on the stationary member for receiving the optical beam; and
   a mirror disposed on the stationary member, the mirror reflecting the optical beam to the receiving means at all times when the optical beam is incident on the mirror.

14. An optical data link for communicating data between a stationary member and a rotating member, comprising:
   a plurality of laser diodes arranged along a circumference of the rotating member, each of the laser diodes transmitting an optical beam at an angle with respect to the rotating member, the angle being fixed during transmission of the optical beam;
   receiving means disposed at a fixed point on the stationary member for receiving the optical beams; and
   reflecting means disposed on the stationary member for simultaneously reflecting the optical beams transmitted by one or more of the laser diodes to the receiving means at all times when the optical beams are incident on the reflecting means.

15. An X-ray computer tomography apparatus having a radiation source disposed on a rotating member for irradiating an object, a radiation detector disposed on the rotating member such that the object is positioned between the radiation detector and the radiation source for detecting radiation penetrating the object and for generating an electrical signal proportional to the intensity of the detected radiation, and a stationary member, the X-ray computer tomography apparatus comprising:
   a plurality of laser diodes arranged along a circumference of the rotating member, each of the laser diodes converting the electrical signal into an optical beam and transmitting the optical beam therefrom at an angle with respect to the rotating member, the angle being fixed during transmission of the optical beam;
   receiving means disposed on the stationary member for receiving the optical beams; and
   reflecting means disposed on the stationary member for simultaneously reflecting the optical beams transmitted by one or more of the laser diodes to the receiving means at all times when the optical beams are incident on the reflecting means.

16. An optical data link for communicating data between a stationary member and a rotating member, comprising:
   transmitting an optical beam therefrom at an angle with respect to the rotating member, the angle being fixed during transmission of the optical beam;
   receiving means disposed at a fixed point on the stationary member for receiving the optical beam;
   reflecting means disposed on the stationary member for reflecting the optical beam to the receiving means at all times when the optical beam is incident on the reflecting means; and
   focusing means for focusing the optical beam onto the reflecting means.

17. An X-ray computer tomography apparatus having a radiation source disposed on a rotating member for irradiating an object, a radiation detector disposed on the rotating member such that the object is positioned between the radiation detector and the radiation source for detecting radiation penetrating the object and for generating an electrical signal proportional to the intensity of the detected radiation, and a stationary member, the X-ray computer tomography apparatus comprising:
   transmitting means disposed on the rotating member for converting the electrical signal into an optical beam and for transmitting the optical beam therefrom at an angle with respect to the rotating member, the angle being fixed during transmission of the optical beam;
   receiving means disposed on the stationary member for receiving the optical beam;
   reflecting means disposed on the stationary member for reflecting the optical beam to the receiving means at all times when the optical beam is incident on the reflecting means; and
   focusing means for focusing the optical beam onto the reflecting means.

18. An optical data link for communicating data between a stationary member and a rotating member, comprising:
   transmitting means disposed on the rotating member for transmitting an optical beam therefrom at an angle with respect to the rotating member, the angle being fixed during transmission of the optical beam;
   receiving means disposed at a fixed point on the stationary member for receiving the optical beam;
   reflecting means disposed on the stationary member for reflecting the optical beam to the receiving means at all times when the optical beam is incident on the reflecting means; and
   means for selectively adjusting the angle at which the optical beam is transmitted by the transmitting means when the optical beam is not being transmitted.

19. An X-ray computer tomography apparatus having a radiation source disposed on a rotating member for irradiating an object, a radiation detector disposed on the rotating member such that the object is positioned between the radiation detector and the radiation source for detecting radiation penetrating the object and for generating an electrical signal proportional to the intensity of the detected radiation, and a stationary member, the X-ray computer tomography apparatus comprising:

transmitting means disposed on the rotating member for converting the electrical signal into an optical beam and for transmitting the optical beam therefrom at an angle with respect to the rotating member, the angle being fixed during transmission of the optical beam;

receiving means disposed on the stationary member for receiving the optical beam;

reflecting means disposed on the stationary member for reflecting the optical beam to the receiving means at all times when the optical beam is incident on the reflecting means; and means for selectively adjusting the angle at which the optical beam is transmitted by the transmitting means when the optical beam is not being transmitted.

20. A method for communicating data between a stationary member and a rotating member, the method comprising the steps of:

transmitting an optical beam from the rotating member at an angle with respect to the rotating member, the angle being fixed during transmission of the optical beam, the step of transmitting the optical beam including the step of selectively adjusting the angle at which the optical beam is transmitted, either before or after the transmission of the optical beam; and reflecting the optical beam to the stationary member.

* * * * *

UNITED STATES PATENT AND TRADEMARK OFFICE
CERTIFICATE OF CORRECTION

PATENT NO. : 5,229,871

DATED : July 20, 1993

INVENTOR(S) : Robert Czarnek, et al.

It is certified that error appears in the above-indentified patent and that said Letters Patent is hereby corrected as shown below:

On the title page, in the Abstract, line 7, after "ber" insert --,--.

Claim 1, column 9, line 29, change "like" to --link--.

Claim 2, column 9, in equation (2) align first and last lines with middle.

Claim 2, column 9, last line in equation (2), insert --]--.

Claim 3, column 9, in equation (2) align first and last lines with middle.

Claim 3, column 9, last line in equation (2), insert --]--.

Claim 3, column 10, in equation (3) change " $/(\overline{AI} + \overline{AS}) \cdot \overline{V}_n]$ " to -- $/(\overline{AL} + \overline{AS}) \cdot \overline{V}_n]$ --.

Claim 4, column 10, line 23, after "reflecting" insert --means disposed on the stationary member for reflecting--.

Claim 5, column 10, line 26, before "according" insert --apparatus--.

Claim 7, column 10, line 36, after "member" insert --,--.

UNITED STATES PATENT AND TRADEMARK OFFICE
CERTIFICATE OF CORRECTION

PATENT NO. : 5,229,871
DATED : July 20, 1993
INVENTOR(S) : Robert Czarnek, et al.

It is certified that error appears in the above-indentified patent and that said Letters Patent is hereby corrected as shown below:

Claim 16, column 12, line 14, after "transmitting" insert --means disposed on the rotating member for transmitting--.

Signed and Sealed this

Thirteenth Day of September, 1994

Attest:

BRUCE LEHMAN

Attesting Officer

Commissioner of Patents and Trademarks